US00RE45677E

(19) United States
(12) Reissued Patent
Steinemann

(10) Patent Number: US RE45,677 E
(45) Date of Reissued Patent: Sep. 29, 2015

(54) ANTI-GLARE PROTECTION DEVICE

(71) Applicant: OPTREL AG, Wattwill (CH)

(72) Inventor: Lukas Steinemann, Jona (CH)

(73) Assignee: OPTREL AG, Wattwil (CH)

(21) Appl. No.: 14/088,100

(22) Filed: Nov. 22, 2013

Related U.S. Patent Documents

Reissue of:
(64) Patent No.: 8,181,270
Issued: May 22, 2012
Appl. No.: 11/223,166
Filed: Sep. 9, 2005

(51) Int. Cl.
*A61F 9/06* (2006.01)
*G01J 1/20* (2006.01)

(52) U.S. Cl.
CPC . *A61F 9/065* (2013.01); *A61F 9/06* (2013.01); *G01J 1/20* (2013.01)

(58) Field of Classification Search
CPC ..... G01J 1/20
USPC ..... 2/8.2, 8.7, 8.8; 250/201.1
See application file for complete search history.

(56) References Cited

U.S. PATENT DOCUMENTS 4,237,557 A * 12/1980 Gordon ..... 2/8.8
4,241,286 A * 12/1980 Gordon ..... 219/147
4,620,322 A * 11/1986 Eggenschwiler et al. ..... 2/8.8
4,863,244 A 9/1989 Fuerthbauer et al.
4,920,257 A 4/1990 Fuerthbauer et al.
5,444,232 A * 8/1995 Gunz et al. ..... 250/201.1
6,067,129 A * 5/2000 Fergason ..... 349/14
6,070,264 A * 6/2000 Hamilton et al. ..... 2/8.8
6,483,090 B1 * 11/2002 Bae ..... 250/201.1
6,881,939 B1 * 4/2005 Hamilton et al. ..... 250/205
7,026,593 B2 * 4/2006 Hamilton ..... 250/201.1
7,161,116 B2 * 1/2007 Steinemann ..... 219/147
7,161,135 B2 * 1/2007 Fergason ..... 250/221
7,358,472 B2 * 4/2008 Hamilton ..... 250/205
8,119,974 B2 2/2012 Hamilton et al.
2005/0001155 A1 * 1/2005 Fergason ..... 250/221
2005/0133685 A1 6/2005 Hamilton

OTHER PUBLICATIONS

European Standard EN 379:2003+A1, ICS 13.340.20, Apr. 2009.
EN 379, Sep. 2003, Europaische Norm, European Standard, Norme Europeene, ICS, 13.340.20.

* cited by examiner

*Primary Examiner* — Jimmy G Foster
(74) *Attorney, Agent, or Firm* — Oliff PLC

(57) ABSTRACT

An anti-glare protection device for a welding mask includes a transmission control circuit for determining a darkening signal from a control signal, a welding activity detection circuit (6) for detecting a welding activity, based on the output of a first sensor circuit. The welding activity detection circuit is arranged to control, via an activation switch, whether either the darkening signal or a signal corresponding to an undarkened optical filter is input to a filter drive circuit. The filter drive circuit drives a controllable optical filter to a transmission value according to the signal input to the filter drive circuit. A manual input device allows a user to manually adjust a user selected signal. A second sensor circuit determines a sensed signal. A manually operable mode selection switch for selecting either, in a manual mode, the user selected signal or, in an automatic mode, the sensed signal to be used as the control signal to the transmission control circuit.

32 Claims, 3 Drawing Sheets

ANTI-GLARE PROTECTION DEVICE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

FIELD OF THE INVENTION

The invention relates to an anti-glare protection device, preferably for a welding protective mask

BACKGROUND OF THE INVENTION

Glare protection or dazzle protection devices are, for example, used in welding protection masks, helmets or goggles. In order to enhance the safety and productivity of the welder, active electro-optical cells or filter elements are used, which can be driven electronically to a bright and dark state respectively, without the need of mechanical movement. Electro-optical filter devices for glare protection typically comprise a liquid crystal cell or LC-cell which is controlled to block light transmission to a greater or lesser extent when a light sensor detects a light intensity exceeding a predefined threshold level and/or exhibiting certain dynamic properties such as jitter or flickering. Furthermore, electro-optical filter devices are known in the prior art which automatically adjust the filter transmission to the varying brightness conditions encountered in a welding situation.

U.S. Pat. No. 4,620,322 shows an electro-optic welding lens assembly in which a light sensing element for controlling the transmission of a LC filter doubles as a power supply for powering the control circuitry and the LC filter.

In U.S. Pat. No. 4,863,244, a welding lens assembly is disclosed which comprises a manually adjustable transmission with an additional automatic override circuit using a brightness sensor for measuring the amount of light falling on the lens assembly. The welder may set the transmission level manually, but if the amount of light exceeds a predetermined threshold, the transmission of light is automatically reduced, compensating for the excess light.

In U.S. Pat. No. 4,920,257, a light filter with the automatic regulation of transmission is described, in which a first optical sensor is arranged behind the filter element in the radiation direction, and a second sensor is arranged beside or in front of the filter element. A subtraction circuit determines the difference between the two sensor signals. Since the filter, when in a blocking state, stops mainly visible light, but not infrared light, the difference is essentially proportional to the amount of visible light. This reduces the influence of infrared light and corresponding unwanted blocking of the filter by infrared light sources.

US Patent Application Publication 2005/0133685 A1 shows a light shutter assembly with automatic shade level adjustment that uses a phototransistor instead of a diode in its light sensing circuit. The light shutter can be driven to one of a plurality of shade levels.

The European Standard EN 379 regulates the use of automatic welder protecting filters in Europe. It includes among others a specification for automatic welding filters that regulate the Shade Number S as a function of light intensity. Shade Numbers are defined in European Norm EN 169, and similarly in the US standard It is thus in principle known to automatically adjust the transmission to the brightness of the welding scene. However, such products have not met with success, since fully automatic filters are only applicable in situations and welding positions where the mask's sensors correctly capture the brightness of the welding process. For other situations, a mask with a manual transmission setting has to be used. Furthermore, in a fully automatic anti-glare device, the welder's specific preference with respect to the perceived brightness is not accounted for.

DESCRIPTION OF THE INVENTION

It is therefore an object of the invention to overcome the limitations of the prior art, and to create an anti-glare protection device of the type mentioned initially that provides increased usability of a welding mask incorporating the anti-glare protection device.

A further object of the invention is to provide an anti-glare protection device with improved protection quality.

These objects are achieved by an anti-glare protection device for a welding mask, comprising a transmission control circuit for determining a darkening signal from a control signal, a welding activity detection circuit for detecting a welding activity, based on a first sensor signal from a first sensor circuit, wherein the welding activity detection circuit is arranged to control, by means of an activation switch, whether either the darkening signal or a signal corresponding to an undarkened optical filter is input to a filter drive circuit. The anti-glare protection device further comprises said filter drive circuit for driving a controllable optical filter to a transmission according to the signal input to the filter drive circuit, a manual input device allowing a user to adjust a user selected signal manually, and a second sensor circuit for determining a sensed signal. A manually operable mode selection switch is provided for selecting either, in a manual mode, the user selected signal or, in an automatic mode, the sensed signal to be used as the control signal to the transmission control circuit.

As a result, a wider range of situations is supported by the mask, including both situations where automatic operation is appropriate, and situations where manual operation is appropriate, e.g. welding positions where the second sensor signal does not correctly represent the brightness of the light emitted by the welding arc.

In a preferred embodiment of the invention, the manual input device is an adjusting knob, e.g. a sliding or rotating knob. The anti-glare protection device may also incorporate an input device for manual fine tuning of the sensed signal when the anti-glare protection device is in automatic mode. In a further preferred embodiment of the invention, the manual input device and the input device for manual fine tuning of the sensed signal are identical.

This gives the possibility to adjust or fine-time the transmission in automatic mode within a small range. In a preferred implementation, this range is limited to +/−1 Shade Numbers (S). This allows the welder to adapt the mask to his personal preference and comfort. As an example, it is a well known fact that older welders prefer a slightly higher filter transmission than younger ones due to the ageing process of the human eye. In a preferred implementation, the same knob as for the adjustment of the S in manual mode is used, reducing complexity and cost for moving parts.

In a further preferred embodiment of the invention, the first sensor signal is determined by a first sensor circuit and the second sensor signal is determined by a second sensor circuit, wherein the first and second sensors circuits differ from one another. The first sensor circuit may comprise a magnetic field sensor, configured to measure a magnetic field caused by the welding activity, or may comprise a current sensor configured to measure a welding current, or an optical sensor configured to measure light emitted by the welding activity. In the latter case, the first and second sensor circuits preferably exhibit a different spectral sensitivity, For example, the first sensor circuit may be particularly sensitive in the UV (ultra-violet) or in the IR (infra-red) range of the spectrum.

In a further preferred embodiment of the invention, the second sensor circuit comprises a light intensity measuring arrangement that measures light over the visible range and weighted according to the spectral sensitivity of the human eye. The spectral sensitivity of the human eye is specified by the so-called V_lambda standard curve well known in spectrometry. This light intensity measuring arrangement may be implemented by a light sensing element whose spectral sensitivity matches that of the human eye, or by a light sensing element in combination with an optical filter, where the spectral sensitivity of the light sensing element combined with the optical filter matches that of the human eye. This optical filter may be made of a synthetic material such as Polycarbonate or PMMA (Polymethylmethacrylate, acrylic glass), incorporating embedded organic or inorganic dying agent.

The dependency of the anti-glare filter transmission as a function of the brightness or light intensity (in automatic mode) preferably includes a minimum value and a maximum value for the transmission. Thus, in the case where welding activity is detected by one or several detectors, but the amount of detected radiation is below the limit for the lowest S for which the mask has been designed, a minimum shade number is ensured. For an exemplary mask, with unadjusted Shade Numbers ranging from 9 to 13, the S including fine-tuning adjustment never drops below 8 when welding is detected. On the other hand, when the amount of radiation is above the limit for the highest S for which the mask has been designed, the S never goes above a certain limit. For the above example mask, the S including fine-tuning adjustment never rises above 14.

In a preferred embodiment of the invention, in automatic mode, upon detection of welding activity by the welding activity detection circuit, the filter transmission is limited to a predetermined maximum by means of an offset signal combined with the output of the second sensor signal. The filter transmission is limited to a predetermined minimum by driving the second sensor circuit into saturation when its input reaches a level corresponding to said transmission minimum.

In yet a further preferred embodiment of the invention, at least one of the first and second sensor circuits comprises a plurality of sensing elements, e.g. an array of photodiodes or a CCD-array or CMOS-array, and is configured to use the maximum value returned by all its sensing elements. This allows to operate correctly even under conditions where only one of the sensing elements is reached by the welding light, thus extending the range of operation of the welding mask. Alternatively, an average value may be used.

The method for controlling the operation of an anti-glare protection device, comprises the steps of a transmission control circuit determining a darkening signal from a control signal;

a first sensor circuit emitting a first sensor signal, and a welding activity detection circuit detecting a welding activity based on said first sensor signal;

the welding activity detection circuit controlling, by means of an activation switch, whether either the darkening signal or a signal corresponding to an undarkened optical filter is input to a filter drive circuit, said filter drive circuit driving a controllable optical filter to a transmission value according to the signal input to the filter drive circuit, a manually operable mode selection switch selecting either, in a manual mode, a user selected signal adjusted by a manual input device, or, in an automatic mode, a sensed signal from a second sensor circuit; and using the signal selected by the mode selection switch as the control signal to the transmission control circuit.

In a preferred embodiment of the invention, the method further comprises the step of adjusting by means of the same manual input device, when in manual mode, the user selected signal, and, when in automatic mode, an offset to the darkening signal.

Further preferred embodiments are evident from the dependent patent claims. Features of the method claims may be combined with features of the device claims and vice versa.

BRIEF DESCRIPTION OF THE DRAWINGS

The subject matter of the invention will be explained in more detail in the following text with reference to preferred exemplary embodiments which are illustrated in the attached drawings, in which.

The reference symbols used in the drawings, and their meanings, are listed in summary form in the list of reference symbols. In principle, identical parts are provided with the same reference symbols in the figures.

DETAILED DESCRIPTION OF PREFERRED EMBODIMENTS

Figure 1:
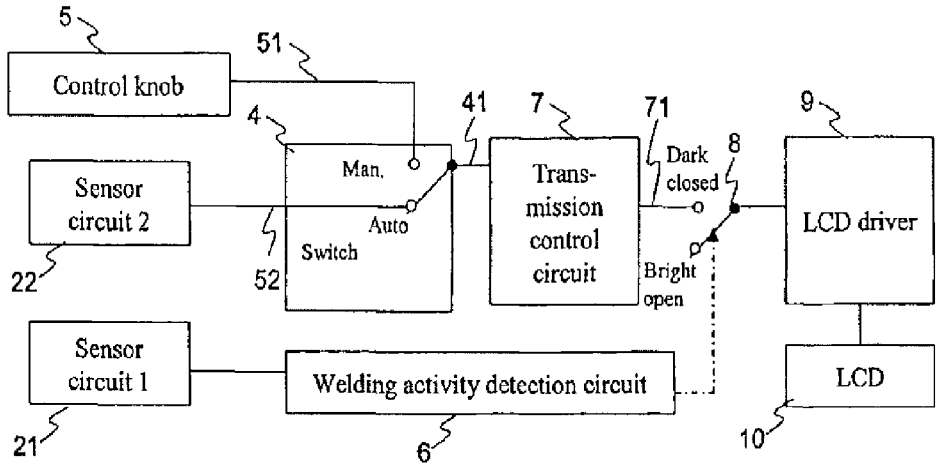
FIG. 1 shows a block diagram of the function.

FIG. 1 shows a block diagram of the function of an anti-glare protection device 1 according to the invention. The output of a first sensor circuit 21 is fed to a welding activity detection circuit 6 which determines whether a welding activity is taking place or not. The nature of the welding activity detection circuit 6 depends on the type of the first sensor circuit 21. For example, if the first sensor circuit 21 comprises an optical sensor, the welding activity detection circuit 6 preferably incorporates a flicker detection circuit which distinguishes the typical welding flicker from ambient light fluctuations. On the other hand, if the first sensor circuit 21 comprises a magnetic field sensor, or a current sensor measuring the welding current, then the welding activity detection circuit 6 for example comprises a noise filter and a threshold circuit.

The output of the second sensor circuit 22 is fed to a mode selection switch 4 which allows to select either said output or a user selected signal 51 provided by a user input device such as an adjusting knob 5. Depending on the position of the mode selection switch 4, either the output of the second sensor circuit 22 or the user selected signal 51 is forwarded as a control signal 41 to a transmission control circuit 7. The user selected signal 51 is set by manual operation of the user input device, which may be a sliding or rotating knob, or a toggle switch or seesaw switch with associated circuitry for storing and varying an analog value. The activation switch 8 is preferably implemented by solid state circuits, while the mode selection switch 4 is preferably implemented by a mechanical switch which can be manually operated.

The transmission control circuit 7 adapts the control signal 41 according to the voltage requirements of the LC cell and hence determines a darkening signal 71.

The output of the welding activity detection circuit 6 determines, by means of an activation switch 8, whether the darkening signal 71 is forwarded to a filter drive circuit 9. The filter drive circuit 9 serves as power stage and drives an optical filter 10 to the transmission (or, to put it the other way round, the darkness) determined by the darkening signal 71.

In another preferred embodiment of the invention, the sensor circuits 21 and 22 comprise one or multiple sensors providing a single output signal, which is used both by the welding activity detection circuit 6 and by the transmission control circuit 7 (the latter depending on the position of the mode selection switch 4).

Figure 2:
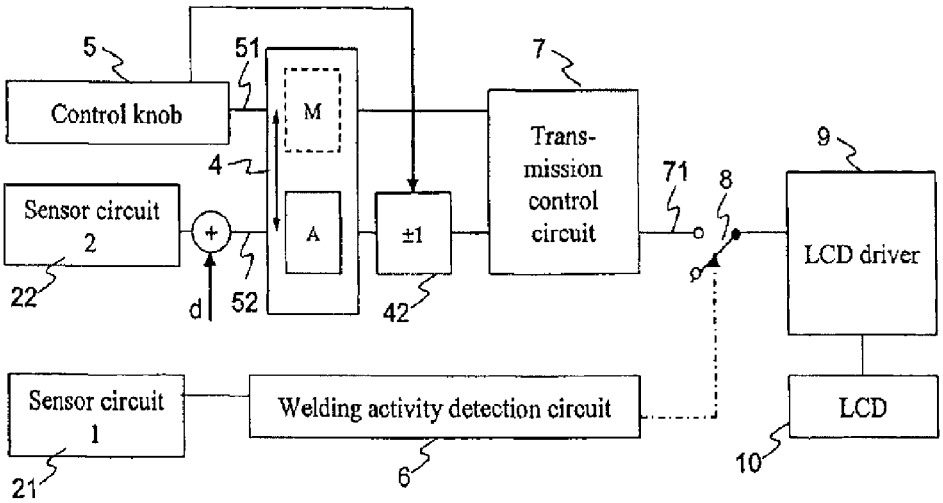
FIG. 2 schematically shows the structure of an anti-glare protection device according to a preferred embodiment of the invention.

FIG. 2 schematically shows the structure of an anti-glare protection device according to another preferred embodiment of the invention. In addition to the elements already described with regard to FIG. 1, a fine tuning circuit 42 is shown. The fine tuning circuit 42 allows to add or subtract a signal value corresponding to one Shade Number to/from the sensed signal 52 before the sensed signal 52 is provided to the transmission control circuit 7. This allows the user to adapt, within safe limits, the automatically determined darkening level to personal preferences. In a preferred embodiment of the invention, this adaptation is done by means of the same adjusting knob 5 that is used to set the darkening level in manual mode. For this reason, the mode selection switch 4 is drawn in a different configuration than in FIG. 1. In manual mode (M), the signal from the adjusting knob 5 is passed to the transmission control circuit 7. In automatic mode (A) the sensed signal 52 output by the second sensor circuit 22 is passed, via the fine tuning circuit 42, to the transmission control circuit 7. The fine tuning circuit 42 may of course also be arranged, seen in the direction of the signal flow, prior to the mode selection switch 4.

In order to ensure that the transmission of the optical filter 10 never drops under a predetermined minimum, a minimum offset d is combined with the signal of the second sensor circuit 22. The same effect on the optical filter 10 transmission may of course be implemented at a later stage of the signal flow. In a preferred embodiment of the invention, the signal of the second sensor circuit 22 and the offset d are combined by means of a maximum function, i.e. a circuit that outputs the largest of its input values. In another preferred embodiment, an amplifier in the sensor circuit is adjusted to work around a predetermined operating point such that the range of brightness relevant for the application such as welding is covered, and values under the lower brightness limit give an amplifier output of zero. The minimum offset d corresponding to the minimum filter transmission is then simply added to the amplifier output, resulting in the left part of the trajectory of FIG. 3, as explained below.

On the other hand, in order to ensure that the optical filter 10 never exceeds a maximum Shade Number, the second sensor circuit 22 is driven into its saturation at a predetermined level of its input. This has effect of limiting the perceived brightness at later stages of the signal flow, and in consequence limits the darkening of the optical filter 10.

Figure 3:
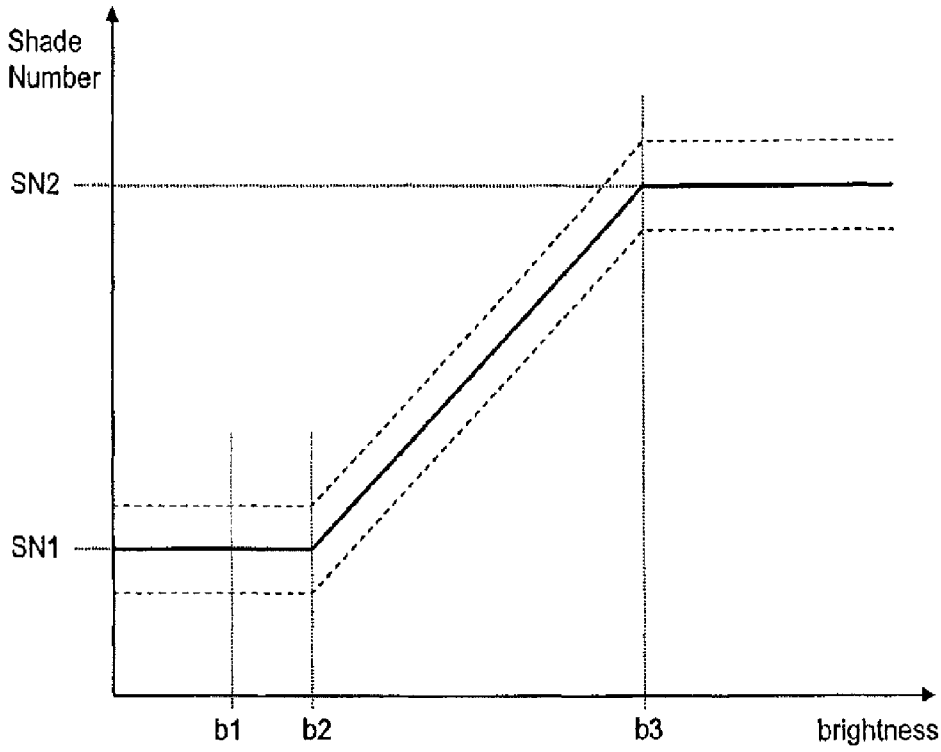
FIG. 3 shows a characteristic curve of the device's operation.

FIG. 3 shows a characteristic curve of the device's operation in automatic mode: The horizontal axis represents a perceived brightness level, typically represented by the output of the second sensor circuit 22. The vertical axis represents the Shade Number to which the optical filter 10 is set. The drawn out black line shows the standard dependency of Shade Number on brightness. Starting with zero brightness, the transmission control circuit 7 outputs a darkening signal 71 corresponding to a predetermined minimum Shade Number S1 of the optical filter 10. For increasing brightness, the darkening signal 71 remains essentially constant at this level. Whether this darkening signal 71 is actually used to control the optical filter 10 is determined by the position of the activation switch 8 controlled by the welding activity detection circuit 6. For example, this may happen when the brightness reaches a threshold b1, or when a flicker circuit or magnetic field sensing arrangement detects a welding activity.

When the brightness increases over a second threshold b2, the Shade Number begins to increase at least approximately linearly with brightness. After a third threshold b3 is reached or exceeded, the Shade Number remains at a predetermined maximum value S2.

In order to allow the welder to adapt the Shade Number to his eyes, the fine tuning circuit 42 allows to modify the Shade Number continuously by at most one Shade Level, both up or down. The two dashed lines of FIG. 3 show the resulting maximum upper and minimum lower trajectories of the Shade Number in function of brightness.

Figure 4:
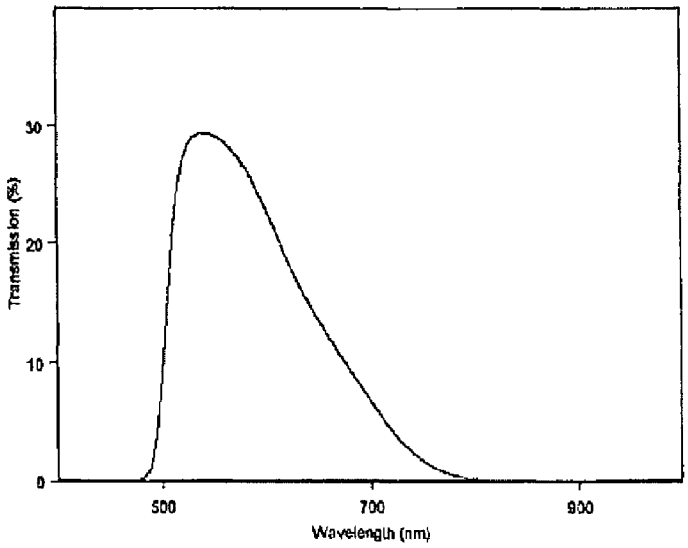
FIG. 4 shows a transmission curve of an optical sensor filter.
Figure 5:
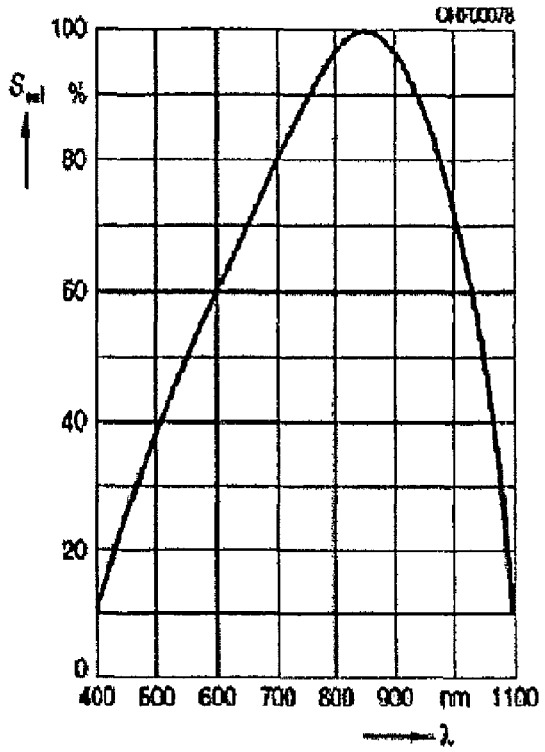
FIG. 5 shows a sensitivity curve of an optical sensor.
Figure 6:
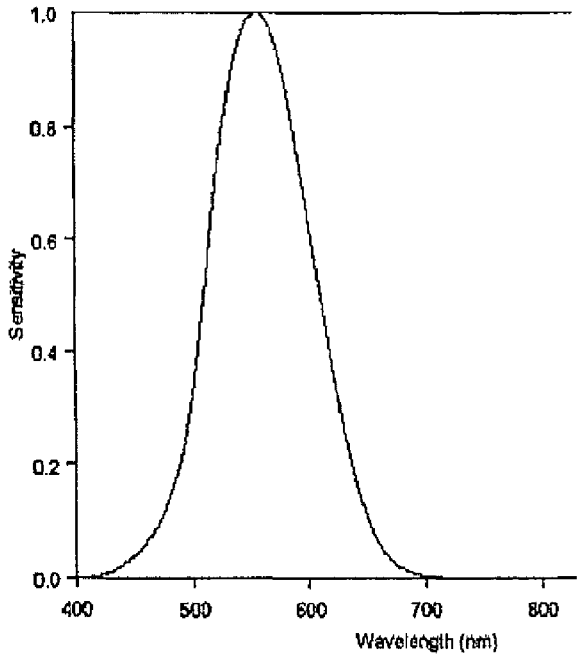
FIG. 6 shows a total sensitivity curve of said sensor combined with said filter.

In a preferred embodiment of the invention, the second sensor circuit 22 comprises a light sensing element whose spectral sensitivity matches that of the human eye. Commercially available sensor units with such a spectral sensitivity are essentially available as entire units with built in circuitry. Since the application in a welding mask requires extremely low power consumption, it may be necessary to custom-build the sensors contained in the second sensor circuit 222. The desired spectral sensitivity is preferably obtained by combining a sensor such as a photodiode, having a first spectral sensitivity, with a filter having a second spectral sensitivity, such that the spectral sensitivity of the photodiode receiving light through the filter is at least close to the spectral sensitivity of the human eye. For example, FIG. 4 shows a transmission curve of an optical sensor filter, FIG. 5 shows a sensitivity curve of an optical sensor, and FIG. 6 shows a total sensitivity curve of said sensor combined with said filter.

In further preferred embodiments of the invention, the first sensor circuit 21 comprises a first sensor whose signals are captured and amplified by a first amplifier, resulting in the signal fed to the welding activity detection circuit 6, and a the second sensor circuit 22 comprises a second sensor 22 whose signals are captured and amplified by a second amplifier 32, resulting in the sensed signal. In an alternative embodiment, the first and second sensor are physically identical, and optionally the first and second amplifier are physically identical as well. That is, there is only one sensor (and optionally only one amplifier) that serves both for providing a signal to the welding activity detection circuit 6 and the mode selection switch 4.

While the invention has been described in present preferred embodiments of the invention, it is distinctly understood that the invention is not limited thereto, but may be otherwise variously embodied and practised within the scope of the claims.

LIST OF DESIGNATIONS

1 anti-glare protection device
21 first sensor circuit
22 second sensor circuit
33 offset
4 mode selection switch

41 control signal
42 fine tuning circuit
5 adjusting knob
51 user selected signal
52 sensed signal
6 welding activity detection circuit
7 transmission control circuit
71 darkening signal
8 activation switch
9 filter drive circuit
10 optical filter

The invention claimed is:

1. An anti-glare protection device for a welding mask, comprising:

a transmission control circuit for determining a darkening signal from a control signal, a filter drive circuit for driving a controllable optical filter to a transmission value according to the signal input to the filter drive circuit, a welding activity detection circuit for detecting a welding activity, based on a first sensor signal from a first sensor circuit with at least one first sensor, wherein the welding activity detection circuit is arranged to control, via an activation switch, whether either the darkening signal from the transmission control circuit or a signal corresponding to an undarkened optical filter is input to the filter drive circuit, a manual input device allowing a user to adjust a user selected signal manually, a second sensor circuit with at least one second sensor for determining a sensed signal, wherein the second sensor circuit differs from the first sensor circuit, and a manually operable mode selection switch with a first signal input for the user selected signal and a second signal input for the sensed signal from the second sensor circuit unit for selecting either, in a manual mode, the user selected signal or, in an automatic mode, the sensed signal to be used as the control signal, and with a signal output for the control signal to the transmission control circuit for determining the darkening signal from the control signal.

2. The anti-glare protection device according to claim 1, wherein the mode selection switch is a manually operable mechanical switch.

3. The anti-glare protection device according to claim 1, wherein the manual input device is an adjusting knob.

4. The anti-glare protection device according to claim 1, further comprising an input device for manual fine tuning of the darkening when the anti-glare protection device is in the automatic mode.

5. The anti-glare protection device according to claim 4, wherein the manual input device and the input device for manual fine tuning of the darkening are identical.

6. The anti-glare protection device according to claim 1, wherein the first and second sensor circuits comprise at least one electromagnetic radiation sensor, and wherein the first and the second sensor circuits exhibit a different spectral sensitivity.

7. The anti-glare protection device according to claim 1, wherein at least one of said at least one first sensor and said at least one second sensor is a magnetic field sensor.

8. The anti-glare protection device according to claim 1, wherein the second sensor circuit comprises a light intensity measuring arrangement that measures light over a visible range and weighted according to a spectral sensitivity of a human eye.

9. The anti-glare protection device according to claim 8, wherein the second sensor circuit comprises at least one light sensing element whose spectral sensitivity matches the spectral sensitivity of the human eye.

10. The anti-glare protection device according to claim 8, wherein the second sensor circuit comprises at least one light sensing element and at least one optical filter, where a spectral sensitivity of the light sensing elements combined with the optical filters results in an overall spectral sensitivity that matches the spectral sensitivity of the human eye.

11. The anti-glare protection device according to claim 1, wherein, in the automatic mode, upon detection of welding activity by the welding activity detection circuit, the filter transmission is limited to a predetermined maximum via an offset signal combined with the output of the second sensor circuit.

12. The anti-glare protection device according to claim 1, wherein, in the automatic mode, upon detection of welding activity by the welding activity detection circuit, filter transmission is limited to a predetermined minimum by driving the second sensor circuit into saturation when its input reaches a level corresponding to said transmission minimum.

13. The anti-glare protection device according to claim 1, wherein at least one of the first and second sensor circuits comprises a plurality of sensing elements and is configured to use one of a maximum or minimum value returned by at least one of the plurality of sensing elements.

14. The anti-glare protection device according to claim 1, wherein, at least one of the first and second sensor circuits comprises a plurality of sensing elements and is configured to use an average value returned by at least one of the plurality of sensing elements.

15. The anti-glare protection device according to claim 13, wherein the plurality of sensing elements is selected from the group consisting of: an array of photodiodes, a CCD-array, and a CMOS detector array.

16. An anti-glare protection device for a welding mask, comprising a transmission control circuit for determining a darkening signal from a control signal, a welding activity detection circuit for detecting a welding activity, based on a first sensor signal, wherein the first sensor signal is determined by a first sensor circuit, a filter drive circuit for driving a controllable optical filter to a transmission *value* according to a signal input to the filter drive circuit, wherein the welding activity detection circuit is arranged to control, via an activation switch, whether either the darkening signal or a signal corresponding to an undarkened optical filter is input to the filter drive circuit, a manual input device allowing a user to adjust a user selected signal manually, a second sensor circuit determining a sensed signal, wherein the second sensor circuit is not identical to the first sensor circuit, and comprising a light intensity measuring arrangement that measures light over a visible range and weighted according to a spectral sensitivity of a human eye, and a manually operable mode selection switch for selecting either, in a manual mode, the user selected signal or, in an automatic mode, the sensed signal to be used as the control signal to the transmission control circuit.

17. A method for controlling the operation of an anti-glare protection device, comprising the steps of:

providing an anti-glare protection device having a transmission control circuit, a filter drive circuit, a welding activity detection circuit, a first sensor circuit, a manual input device, a second sensor circuit, and a manually operable mode selection switch;

determining a darkening signal from a control signal;

detecting a welding activity based on the output of said first sensor circuit;

controlling, via an activation switch, whether either the darkening signal from the transmission control circuit or a signal corresponding to an undarkened optical filter is input to a filter drive circuit, driving a controllable optical filter to a transmission value according to the signal input to the filter drive circuit, selecting either, in a manual mode, a user selected signal adjusted by a manual input device, or, in an automatic mode, a sensed signal from a second sensor circuit, and using the signal selected by the mode selection switch as the control signal, and with a signal output for the control signal to the transmission control circuit for determining the darkening signal from the control signal.

18. The method of claim 17, comprising the further step of:

adjusting, via the manual input device, when, in manual mode, the user selected signal, and, when, in automatic mode, an offset to the darkening signal.

*19. A welding mask including the anti-glare protection device according to claim 16.*

*20. A welding mask including the anti-glare protection device according to claim 1.*

*21. An anti-glare protection device for a welding mask, comprising:*

*a welding activity detection circuit that detects welding activity, based on output from at least one first sensor,*

*a brightness level detection circuit that outputs a signal based on a perceived brightness level signal from at least one second sensor,*

*a transmission control circuit that automatically determines and outputs a darkening signal, the darkening signal indicating a degree of darkening corresponding to the perceived brightness level signal,*

*a filter drive circuit that (i) controls a controllable optical filter to be in an undarkened state if the welding activity detection circuit does not detect welding activity, and (ii) automatically controls the optical filter to be in a darkened state at the degree of darkening indicated by the darkening signal if the welding activity detection circuit detects welding activity, and*

*an input device for manual fine tuning of the degree of darkening.*

*22. The anti-glare protection device according to claim 21, wherein the first sensor and the second sensor are the same sensor.*

*23. The anti-glare protection device according to claim 21, wherein the first sensor and the second sensor are different sensors.*

*24. The anti-glare protection device according to claim 21, wherein the output from the at least one first sensor is a sensor signal.*

*25. The anti-glare protection device according to claim 21, further comprising the first sensor.*

*26. The anti-glare protection device according to claim 25, further comprising the second sensor.*

*27. The anti-glare protection device according to claim 21, wherein the input device for manual fine tuning is an adjusting knob.*

*28. A welding mask including the anti-glare protection device according to claim 21.*

*29. A method for controlling the operation of an anti-glare protection device that has a transmission control circuit, a filter drive circuit, a brightness sensor circuit, and an input device for manual fine tuning, the method comprising the steps of:*

*detecting a perceived brightness level based on the output of the brightness sensor circuit;*

*automatically controlling a degree of darkening of a darkened state of a controllable optical filter, the degree of darkening corresponding to the perceived brightness level; and*

*adjusting the degree of darkening based on manual fine tuning input from the input device.*

*30. The method of claim 29, wherein the anti-glare protection device has a welding activity detection circuit, and further comprising automatically driving the controllable optical filter to the darkened state when the welding activity detection circuit detects welding activity.*

*31. An anti-glare protection device for a welding mask, comprising:*

*a welding activity detection circuit that detects welding activity, based on output from at least one first sensor,*

*a brightness level detection circuit that outputs a signal that is based on a perceived brightness level signal from at least one second sensor,*

*a manual input device that allows a user to adjust a user-selected signal manually,*

*a manually operable mode selection switch for selecting, as a signal to be output, either (i) in a manual mode, the user-selected signal or (ii) in an automatic mode, the signal that is based on the perceived brightness level,*

*a transmission control circuit that outputs a darkening signal corresponding to the signal selected by way of the mode selection switch, and*

*a filter drive circuit that (i) controls a controllable optical filter to be in an undarkened state if the welding activity detection circuit does not detect welding activity, and (ii) automatically controls the optical filter to be in a darkened state at a transmission value based on the darkening signal if the welding activity detection circuit detects welding activity.*

*32. A welding mask including the anti-glare protection device according to claim 31.*

* * * * *